United States Patent
Olson

(10) Patent No.: US 10,555,733 B2
(45) Date of Patent: Feb. 11, 2020

(54) COLORED SUTURE CONSTRUCTION

(71) Applicant: Teleflex Medical Incorporated, Morrisville, NC (US)

(72) Inventor: James R. Olson, Norwich, CT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 341 days.

(21) Appl. No.: 15/332,485

(22) Filed: Oct. 24, 2016

(65) Prior Publication Data

US 2017/0035418 A1 Feb. 9, 2017

Related U.S. Application Data

(62) Division of application No. 14/031,654, filed on Sep. 19, 2013, now Pat. No. 9,474,520, which is a division
(Continued)

(51) Int. Cl.
*A61L 17/00* (2006.01)
*A61B 17/06* (2006.01)
(Continued)

(52) U.S. Cl.
CPC ........ *A61B 17/06166* (2013.01); *A61B 17/04* (2013.01); *A61L 17/04* (2013.01);
(Continued)

(58) Field of Classification Search
CPC ... A61B 17/06; A61B 17/06166; A61B 17/04; A61B 2017/00004; A61B 2017/06176; A61B 2017/06171; A61L 17/00
See application file for complete search history.

(56) References Cited

U.S. PATENT DOCUMENTS 3,949,755 A 4/1976 Vauquois
6,994,719 B2 2/2006 Grafton
(Continued)

FOREIGN PATENT DOCUMENTS

CA 2509871 A1 12/2005
EP 1293218 3/2003
(Continued)

OTHER PUBLICATIONS

Second Chinese Office Action dated Feb. 16, 2017, for Chinese Patent Application No. 201510475820.0.
(Continued)

*Primary Examiner* — Vi X Nguyen
(74) *Attorney, Agent, or Firm* — Baker & Hostetler LLP

(57) ABSTRACT

A suture made of a woven braid of fibers is provided. The suture includes: at least one first end; at least one second end comprising a colorable material wherein the second end has been colored a single color along an entire length of the second end; and at least one third end comprising a colorable material wherein only a portion of the third end is colored a continuous color. In another embodiment, a method of manufacture of a suture is provided. The method includes: braiding an elongate suture from a first end, a second end comprising a colorable material, and a third end comprising a colorable material; coloring the second end a single first color along an entire length of the second end; coloring only a first portion of the third end a second color.

26 Claims, 4 Drawing Sheets

Related U.S. Application Data of application No. 12/767,127, filed on Apr. 26, 2010, now Pat. No. 8,632,566.

(60) Provisional application No. 61/172,989, filed on Apr. 27, 2009.

(51) Int. Cl.
    *A61L 17/04*     (2006.01)
    *A61L 17/14*     (2006.01)
    *D07B 1/02*     (2006.01)
    *D07B 1/14*     (2006.01)
    *A61B 17/04*     (2006.01)

(52) U.S. Cl.
CPC .............. *A61L 17/14* (2013.01); *D07B 1/025* (2013.01); *D07B 1/148* (2013.01); *A61B 2017/06171* (2013.01); *D07B 2201/1096* (2013.01); *D07B 2201/209* (2013.01); *D07B 2205/2014* (2013.01)

(56) References Cited

U.S. PATENT DOCUMENTS

| | | |
|---|---|---|
| 7,892,256 B2 | 2/2011 | Grafton et al. |
| 8,012,172 B2 | 9/2011 | Grafton et al. |
| 2003/0139775 A1 | 7/2003 | Grafton |
| 2005/0192631 A1* | 9/2005 | Grafton .............. A61B 17/06166 606/228 |
| 2006/0155329 A1 | 7/2006 | Grafton et al. |
| 2010/0075020 A1* | 3/2010 | Reinprecht .............. D06B 3/04 427/2.31 |

FOREIGN PATENT DOCUMENTS

| | | |
|---|---|---|
| JP | 4504585 B2 | 7/2010 |
| JP | 4667853 B2 | 4/2011 |

OTHER PUBLICATIONS

Chinese Office Action dated Mar. 29, 2013 for Chinese Patent Application No. 201010159627.3.
Japanese Office Action dated Feb. 28, 2013 for Japanese Patent Application No. 2010-115776.
Office Action dated Jan. 20, 2015, in corresponding Canadian Application No. 2,701,546.
Office Action issued in corresponding Chinese Application No. 201310681156.6.
Office Action dated Feb. 19, 2014 in corresponding Canadian Appl. No. 2,701,546.
Office Action issued in corresponding Japanese Application No. 2010-115776.
US Office Action dated Jan. 14, 2016, in U.S. Appl. No. 14/031,654.
Chinese Office Action dated Jan. 24, 2017, for Chinese Patent Application No. 201310681156.6.

\* cited by examiner

COLORED SUTURE CONSTRUCTION

CROSS REFERENCE TO RELATED APPLICATION

This application is a divisional application of pending application Ser. No. 14/031,654, filed Sep. 19, 2013, which is a divisional application of application Ser. No. 12/767, 127, filed Apr. 26, 2010, now U.S. Pat. No. 8,632,566, which claims priority to earlier filed U.S. Provisional Application No. 61/172,989, filed on Apr. 27, 2009. This application claims priority to the above mentioned applications and the disclosures of which are hereby incorporated by reference, in their entirety.

FIELD OF THE INVENTION

The present invention generally relates to a suture. More particularly, the present invention pertains to a colored construction for sutures.

BACKGROUND OF THE INVENTION

Sutures are commonly used to hold together tissue that has been severed by injury, incision, or surgery to aid in the healing process or to apply pressure to blood vessels to stop bleeding. Sutures can be absorbable or non-absorbable. Non-absorbable sutures are made from inherently colorless materials such as silk, polypropylene, polyester, nylon, or ultra high molecular weight polyethylene (UHMWPE). Sutures are commonly in either braided multifilament or monofilament construction, but are sometimes also known in a twisted construction. The form of a suture is usually dictated by the stiffness or fiber modulus of its constituent fiber. Sutures require good pliability for their handling and knotting properties. Thus, fibers that are too stiff cannot be used in a monofilament form for larger suture sizes but rather in bundles of small denier filaments. These strands of multifilament are then braided together to form a suture. As the suture diameter gets larger, a core is usually added inside the braided sheath. Fibers with a modulus below about 600,000 psi can be used in monofilament form, although lower modulii are preferred. Thus, polyester and UHMWPE sutures are used in multifilament braids, while polypropylene is used as a monofilament suture. Some materials like nylon 66 with borderline properties are made in both multifilament and monofilament constructions. Natural fibers like silk that are fine denier can only be used in multifilament constructions.

Synthetic and most natural materials used to make sutures are without color. With the two basic constructions of braided multifilament and monofilament many types of sutures would be indistinguishable from other sutures even though their properties might be quite different. Thus, the value of coloring in sutures has long been recognized. Not only does color provide distinction between different types of sutures but is also known to aid the surgeon to keep track of sutures in the blood field during surgery.

Sutures are implantable devices and only specific colorants listed in the Code of Federal Regulations (CFR) for a particular suture material can be used. The regulations also put a limit on the maximum weight percent for each colorant for each suture material. Thus, there are limitations in colors available for all suture materials. There are also certain inherent limitations to how color can be added to some suture materials based on their polymer properties and how they are processed into sutures.

The advent of endoscopic surgery procedures has put additional pressure on surgeons to correctly identify sutures and their respective ends for proper tying of knots in confined spaces. During suturing it may be necessary for a physician to distinguish between the ends of similar sutures, which becomes more difficult when both ends of the sutures have an identical appearance of either no color or the same color.

One way to aid a surgeon in distinguishing an incoming end from an outgoing end of a suture, is to use a "half and half" suture, in which one half or one end is colored and the other half or end remains white. For example, Teleflex Medical of 1295 Main Street, Coventry, Conn. 06238, has made a polyester braided tape since 1998 in which one half of it has been dyed with D&C Green No. 6. So the tape has one end that is green and one end that is undyed white. However, a suture made from white UHMWPE yarn is not dyeable owing in part to the high crystallinity of the fiber and therefore cannot be dip dyed to distinguish one side from the other. To add color to a colorless braid of UHMWPE, it is therefore necessary to incorporate either a monofilament or a multifilament of a dyeable fiber material into the braided suture construction. This construction can then be immersed half way into a dye bath that will only color the dyeable fiber and not the UHMWPE fiber. Although it is highly unusual to co-braid a monofilament with multifilament yarn in a suture construction, monofilaments can be used for this application as they can bring a brighter color to the overall braid.

Although the half and half does allow the surgeon to distinguish between the incoming and outgoing ends of one individual suture strand, it offers no help when two or more of the same type of suture is being used. In these cases, there is no differentiation between the various incoming and outgoing ends of suture from each other.

Additionally, while the ends are distinguishable in an individual half and half suture, one half of the suture remains white and there can still be considerable white glare observed under bright lights, such as those used in endoscopic surgery. It is therefore also necessary to reduce the glare on the colorless portions of these sutures.

Accordingly, it is desirable to provide a UHMWPE suture which has distinguishable ends, a distinct junction, and has a reduced glare in the surgical field.

SUMMARY OF THE INVENTION

The foregoing needs are met, to a great extent, by the present invention, wherein in some embodiments a suture that is capable of overcoming the disadvantages described herein at least to some extent is provided.

In accordance with an embodiment of the present invention, a suture includes an elongate woven braid of filaments. The elongate woven braid of filaments is made up of one or more first ends of ultra-high molecular weight polyethylene (UHMWPE). At least one second end is made from a colorable material. The at least one second end is a single continuous color. At least one third end is made from a dyeable material. The at least one third end is dyed a continuous color for a portion of its length for any one colorant.

In accordance with another embodiment of the present invention, a suture includes an elongate woven braid of filaments. The elongate woven braid of filaments is made up of at least a first end including ultra-high molecular weight polyethylene (UHMWPE) multi-filament fiber and at least a second made from a dyeable fiber material. The second end is a single continuous first color. At least a third end is made from a dyeable fiber material. At least a first portion of the third end is dyed a continuous second color. The second color can be different from the first color. A second portion of the third end can also be dyed a continuous third color, different from the second color. The third color can also be different from the first color. A junction line between the first portion of the at least one third end and the second portion of the third end is distinct due to an application of an anti-wicking compound during a step in formation of the suture.

In accordance with another embodiment of the present invention, the at least one second end of the suture can be made from a fiber than can be dyed like one of nylon or polyester. The at least one third end can be made from one of polypropylene monofilament, nylon, polyethylene, or polyester. Additionally, the suture can include a core. One half of a length of the elongate woven braid can be dipped into a dye bath to color the at least one third end. Alternately, the elongate woven braid can be dipped into a dye bath to color the third end and to etch the first ends comprising the ultra-high molecular weight polyethylene. A dye used to color the at least one second end can be a mordant dye and the dye used to color the at least one third end is one of an acid, vat or solvent dye. In addition, the braid can include a first color pattern on a first portion of the braid and a second color pattern different from the first color pattern on a second portion of the braid.

In accordance with another aspect of the present invention, a method of manufacture of a suture includes braiding an elongate suture from at least a first end of ultra-high molecular weight polyethylene, at least a second end made from a dyeable material, and at least a third end made from a dyeable material. The method also includes dyeing the second end a single continuous first color and dyeing at least a portion of the third end a continuous second color. The method can also include dyeing the second and third ends before braiding or alternately dyeing the first portion of the third end after the third end is braided into the suture. A second portion of the third end of the suture can be dyed a third continuous color. Additionally, the method can include dipping at least a half of the elongate suture into a dye bath.

In accordance with another aspect of the present invention, a suture made of a woven braid of fibers is provided. The suture includes: at least one first end; at least one second end comprising a colorable material wherein the second end has been colored a single color along an entire length of the second end; and at least one third end comprising a colorable material wherein only a portion of the third end is colored a continuous color.

In accordance with another aspect of the present invention, a method of manufacture of a suture is provided. The method includes: braiding an elongate suture from a first end, a second end comprising a colorable material, and a third end comprising a colorable material; coloring the second end a single first color along an entire length of the second end; coloring only a first portion of the third end a second color.

In accordance with another aspect of the present disclosure, a suture is provided. The suture includes: a woven braid of fibers having: a first material component; a second material component wherein the second material component is a colorable material colored a single color along an entire length of the second material component; and a third material component wherein the third material component is colored a continuous color only along a portion of an entire length of the third material component.

There has thus been outlined, rather broadly, certain embodiments of the invention in order that the detailed description thereof, herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

The present invention provides, in some embodiments, a braided, colored suture construction. The colored suture is an elongate woven braid of filaments including at least a first end made of an ultra high molecular weight polyethylene (UHMWPE). The suture preferably includes several ends of UHMWPE braided together. The ends of UHMWPE are a multifilament fiber as is well known in the art. The braided, colored suture also includes an end made of a material which contains a colorant which can be either a dye or a pigment in a single continuous color, and another end made of a dyeable material of which at least a portion of its length is dyed a different color. Preferably such dyed portion of the different colored end constitutes only half the length of the suture. This invention provides surgeons with improved recognition of suture ends in surgery by construction of a bi-colored co-braid with at least two ends of different colors braided into a UHMWPE construction. One of the colored ends runs continuously from one end of the suture to the other end. The other colored end is colored only on one half of the end. This provides a suture with two distinguishable ends, while still maintaining a continuous line of color along the length of the suture.

Figure 1:
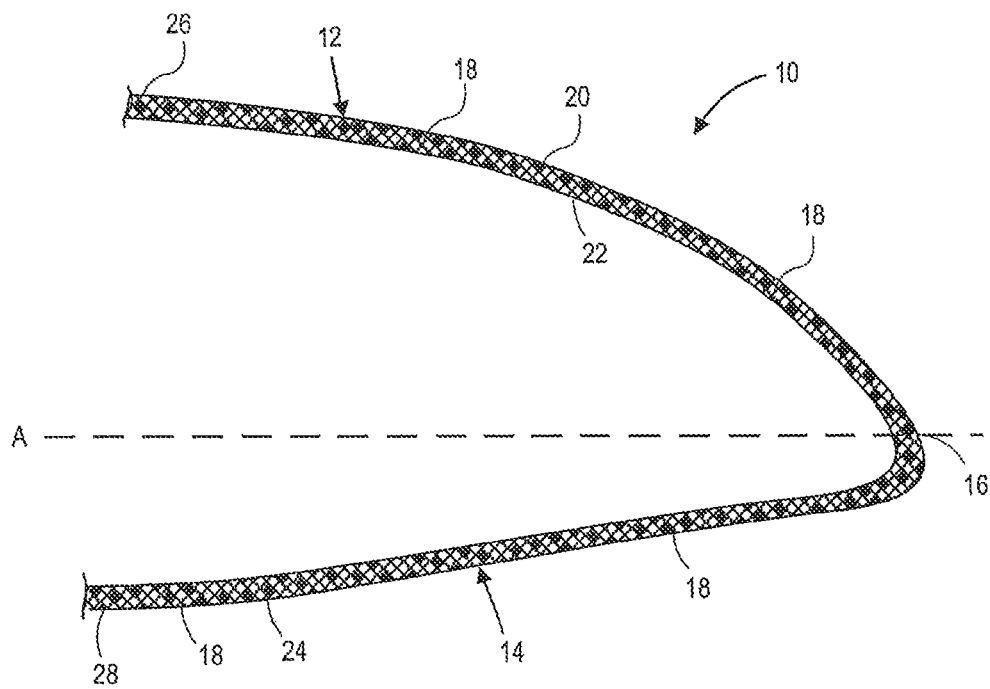
FIG. 1 illustrates a colored suture in accordance with an embodiment of the invention.

The invention will now be described with reference to the drawing figures, in which like reference numerals refer to like parts throughout. FIG. 1 illustrates an end of a braided, colored suture 10 in accordance with the present invention. The braided, colored suture 10 has a first half 12 above axis A and a second half 14 below axis A, as shown in FIG. 1. The point where the first half 12 and the second half 14 meet is a junction 16 of the braided, colored suture 10. In one embodiment, the braided, colored suture 10 can be made from UHMWPE, a material that contains a continuous length of colorant, like for example, polypropylene monofilament with the pigment [phthalocyaninato(2-)] copper and another material that is dyeable, such as nylon or polyester. UHMWPE is generally colorless and is shown in FIG. 1 as colorless regions 18. Additionally, the first half 12 includes colored regions 20 and 22, and the second half 14 includes colored regions 24, which match the color of region 20. These colored regions 20, 22, and 24 are created by including a monofilament or multifilament end materials containing colorants approved for use by the United States Food and Drug Administration (FDA).

Figure 2:
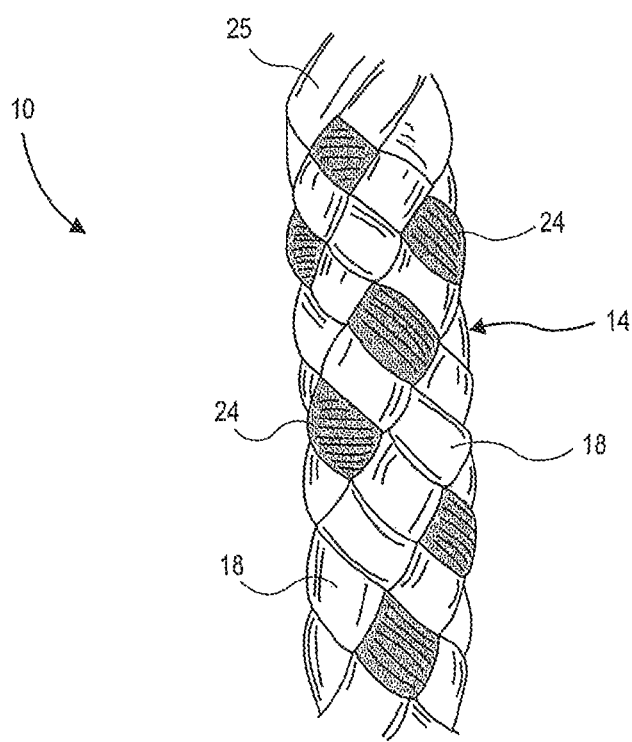
FIG. 2 illustrates a braided colored suture in accordance with an embodiment of the invention.

FIG. 2 illustrates a close-up view of the second half 14 of the braided, colored suture 10, shown in FIG. 1. The braided, colored suture 10 takes the form of an elongate woven braid of ends and has a woven appearance. The ends of the braided, colored suture 10 can be monofilaments or multifilament ends. The ends of the continuous colored material, which is present in both half lengths 12 and 14, are interwoven with the UHMWPE to form colored regions labeled 24. The braided, colored suture 10 can be braided into different patterns depending on the placement of the bobbins holding the ends on the braiding machine. The possible patterns will be discussed further below.

The braided, colored suture 10 illustrated in FIGS. 1 and 2 can be made in one example for a USP size 2 suture by using a sixteen carrier braider to co-braid fourteen ends of a non-colored multifilament UHMWPE yarn 18 with one end of a colored polypropylene monofilament, such as a blue polypropylene monofilament and one end of a clear monofilament nylon. The braided, colored suture 10 is then wound on a frame and the first half 12 is dipped into an FDA approved color bath to color the nylon in the first half 12 to a color such as a dark green. Neither the UHMWPE nor the colored polypropylene will absorb any of the dark green dye. This results in the first half 12 of the braided, colored suture 10 having colorless, blue, and dark green regions, 18, 20, and 22 respectively. The second half 14 of the braided, colored suture 10 has colorless regions 18 and 25 and blue regions 24.

Alternately, as an example of another embodiment, the braided, colored suture 10 illustrated in FIGS. 1 and 2 can be made by using a sixteen carrier braider to co-braid fourteen ends of UHMWPE with one end of a black nylon monofilament that is entirely dyed with logwood extract, an FDA approved colorant, and one end of clear monofilament nylon. A wound frame of the braided, colored suture 10 is then dipped halfway into a dye bath of an FDA approved colorant to color half of the end of the clear nylon. The color is not absorbed by the UHMWPE or the continuous end of black nylon that was already entirely dyed and only half of the colorless nylon is dyed. It appears that since the logwood extract is a mordant dye, it is not displaced by the dye.

Since it has been found that a dye will not affect the black color of nylon dyed with logwood extract, this discovery can be used to prepare two tone half and half sutures of the invention. For example, if the first ends are colorless UHMWPE yarn, the second end a continuous blue polypropylene monofilament and the third end half dyed black monofilament nylon, then a two tone half and half suture is created when this braid is processed in a dye bath. The only portion of the braid that will absorb color is the colorless half of the nylon to give a two tone half and half suture.

As illustrated in FIG. 1, the braided, colored suture 10 made in the manner described above, or made in another similar manner, will have a first half 12 which has a color pattern that is distinguishable from a color pattern on the second half 14. Therefore, a surgeon can distinguish a first end 26 from a second end 28 of the braided, colored suture 10. This prevents confusion and allows for ease and speed of suturing and an overall faster procedure. Having a color pattern on both the first half 12 and the second half 14 of the braided, colored suture 10 also decreases the "white glare" from intense lights used in endoscopic and other surgeries. Additionally, having a color pattern on both the first half 12 and the second half 14 of the braided, colored suture 10 allows a surgeon to easily distinguish the junction 16 of the first half 12 of the braided, colored suture 10 and the second half 14 of the braided colored suture 10. The junction 16 appears more distinct.

Figure 3:
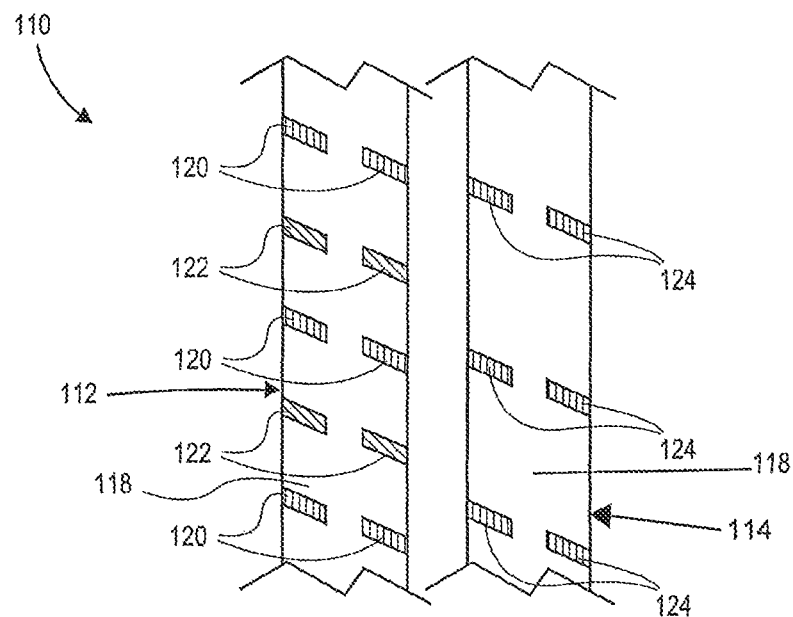
FIG. 3 schematically illustrates an in-line pattern for the colored suture in accordance with an embodiment of the invention.
Figure 4:
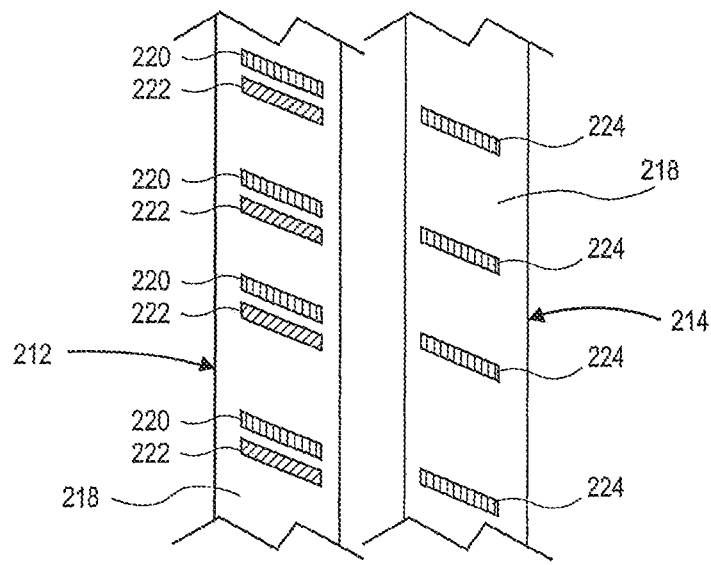
FIG. 4 schematically illustrates a side by side pattern for the colored suture in accordance with an embodiment of the invention.
Figure 5:
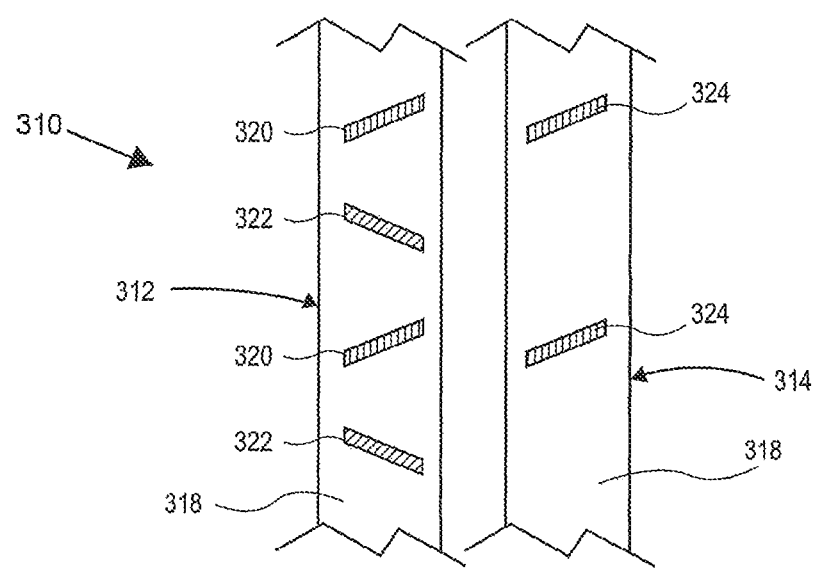
FIG. 5 schematically illustrates a cross pattern for the colored suture in accordance with an embodiment of the invention.

FIGS. 3, 4, and 5 illustrate example patterns such as in-line, side by side, and cross patterns, which are a few of the many patterns that can be made by setting up a braiding machine in different ways. FIG. 3 illustrates an in-line pattern in accordance with an embodiment of the invention. A first half 112 of a braided colored suture 110 has a pattern with two colors and each color is repeated in-line. The field 118 of the suture is made from a braid of UHMWPE ends which are colorless. A first color is represented by areas labeled 120 and a second color is represented by areas labeled 122. The first color is incorporated by using a first co-braided end of a colored material such as nylon or polypropylene. The second color is incorporated by using a second co-braided end of a colorless dyeable material such as nylon which is subsequently dipped for a portion of the length of the suture in a dye or colorant to provide the second color. In this example, a first half 112 of the length of the suture is dipped. The second half 114 of the braided, colored suture 110 has a single colored pattern represented by areas labeled 124, which is the result of the incorporation of the first co-braided end of colored material and matches the color of areas 120. Because the second half 114 of the braided, colored suture 110 is not dipped into a colorant, the other half of the second co-braided end, of colorless dyeable material, remains colorless.

FIG. 4 illustrates a side by side pattern in accordance with an embodiment of the invention. A first half 212 of a braided colored suture 210 has a pattern with two colors side by side. The field 218 of the suture is made from a braid of UHMWPE ends which are colorless. A first color is represented by areas labeled 220 and a second color is represented by areas labeled 222. The first color is above the second color and the two colored regions are generally parallel. The first color is incorporated by using a first co-braided end of a colored material such as nylon or polypropylene. The second color is incorporated by using a second co-braided end of a colorless dyeable material such as nylon which is subsequently dipped for a portion of the length of the suture in a dye or colorant to provide the second color. In this example, one half 212 of the length of the suture is dipped.

The second half 214 of the of the braided, colored suture 210 has a single colored pattern represented by areas labeled 224, which is the result of the incorporation of the first co-braided end of colored material and matches the color of one of the colored areas 220 or 222. Because the second half 214 of the braided, colored suture 210 is not dipped into a colorant, the other half of the second co-braided end, of colorless dyeable material, remains colorless.

FIG. 5 illustrates a cross pattern in accordance with an embodiment of the invention. A first half 312 of a braided colored suture 310 has a pattern with two colors side by side. The field 318 of the suture is made from a braid of UHMWPE ends which is colorless. A first color is represented by areas labeled 320 and a second color is represented by areas labeled 322. The first color areas are at an angle to the second color areas, forming a v-shaped cross pattern. The first color is incorporated by using a first co-braided end of a colored material such as nylon or polypropylene. The second color is incorporated by using a second co-braided end of a colorless dyeable material such as nylon which is subsequently dipped for a portion of the length of the suture in a dye or colorant to provide the second color. In this example, one half 312 of the length of the suture is dipped. The second half 314 of the of the braided, colored suture 310 has a single colored pattern represented by areas labeled 324, which is the result of the incorporation of the first co-braided end of colored material such as a nylon. Because the second half 314 of the braided, colored suture 310 is not dipped into a colorant, the other half of the second co-braided end of colorless dyeable material remains colorless.

Figure 6:
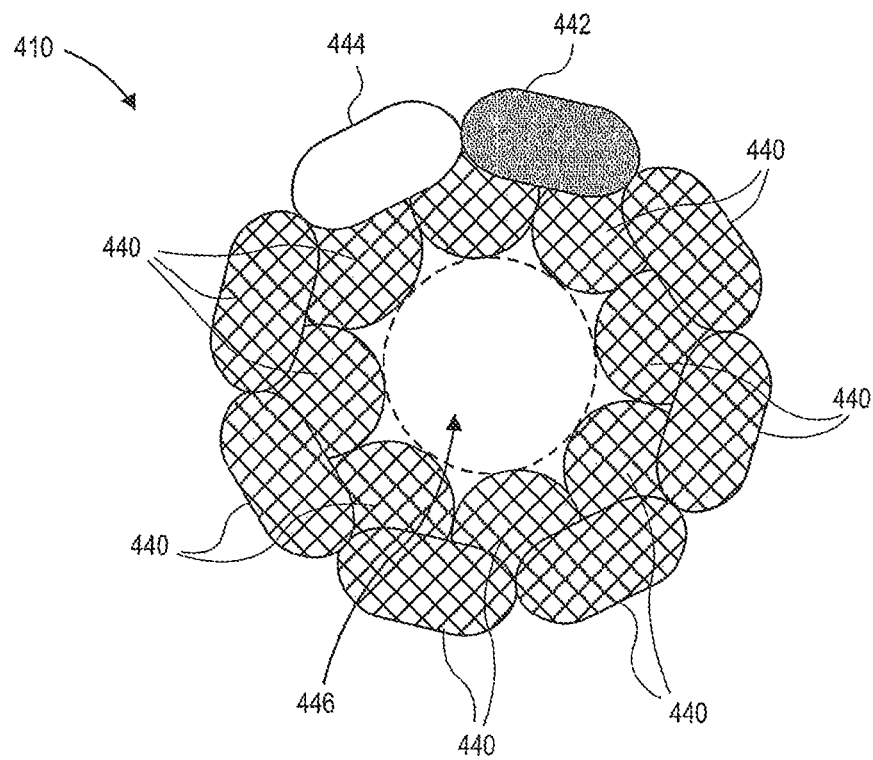
FIG. 6 illustrates a sectional view of a braided, colored suture in accordance with an embodiment of the invention.
Figure 7:
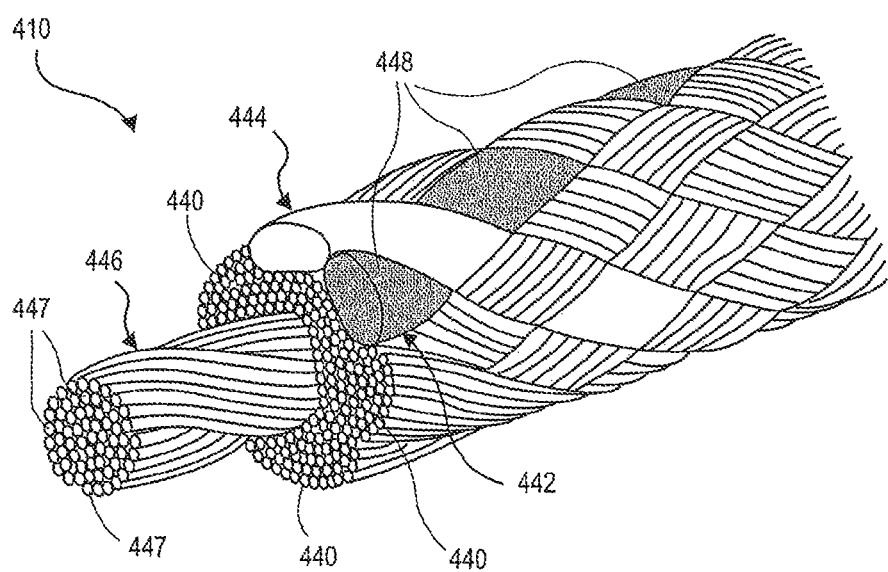
FIG. 7 illustrates a partially sectional view in accordance with an embodiment of the invention.

FIGS. 6 and 7 illustrate a braided, colored suture 410 in accordance with the present invention. The suture 410 includes monofilament or multifilament ends made from materials such as UHMWPE, nylon, or polyethylene. Ends 440 are made from UHMWPE and are generally colorless. End 442 is made from a monofilament or multifilament end of continuously colored nylon or polyethylene. End 444 is made from a monofilament or multifilament of colorless nylon. The braided, colored suture 410 can then be wound on a frame and half dipped into an FDA approved color bath to color half of a length of the nylon end 444 to a color such as a dark green. Additionally, the suture 410 can optionally include a core 446, which can take the form of a multifilament yarn, a monofilament yarn, or a braid of monofilaments or multifilament ends 447. As illustrated in FIG. 7, the end 442 made from the monofilament or multifilament end of continuously colored nylon or polyethylene creates a color pattern 448 on the colored braided suture 410.

In addition to, the color combinations already mentioned other combinations might be envisioned with other approved colorants listed by the FDA for existing suture materials. Thus, the dyes and colored filaments are not limited to those discussed so far. Any suitable FDA approved colorant or colored material can be used. For example, a high density polyethylene monofilament colored with a blue colorant, chromium-cobalt-aluminum oxide, can also be used as the second component containing continuous color. For the third component, polyester (polyethylene terephthalate (PET) or polybutylene terephthalate (PBT)) could also be incorporated into the braided, colored suture and half-dyed.

It is also possible that existing colorants and dyes already approved in colors for one material will eventually be approved for other materials. For example, for the second component, continuous monofilaments of polypropylene monofilament might be colored with D&C Green #6 or D&C Violet #2. For the third component, a multifilament poly-L-lactide (PLLA) absorbable yarn could be incorporated into the braided, colored suture and half-dyed with colorants such as D&C Green #6 or D&C Violet #2. Although neither of these colorants is listed for polypropylene or PLLA suture materials, their safe use in absorbable sutures like PGA where all the contained dye is released is a consideration for their use in other suture materials. Thus, the invention described herein cannot be limited to the current inventory of approved suture materials and listed color colorants, but can be put to practice with newly listed colorants, and approved suture materials.

In addition to substituting one end of a continuous colored fiber and one end of a colorless, but dyeable end into a standard braided construction, this invention can also be put into practice by first co-plying small monofilaments or low denier multifilament of both the second and third component materials into the UHMWPE multifilament braiding bobbins. This optional method is particularly suited for suture sizes that use small carrier braiding machines where the substitution of a lower strength colored material for a high strength material might affect the overall performance properties of the braided suture. For example, a USP size 5-0 high strength suture is braided on a three carrier braider. If one end of the braid is substituted with an end with continuous color and another end with a colorless, but dyeable fiber, then about 67% of the high strength fiber will be lost. This situation is remedied by co-plying the second and third components of the invention into the braider bobbins of the UHMWPE yarn. When this construction is half dyed, it will contain the benefits of this invention. Although this option is directed at braids that contain a small number of ends, it can certainly be used in all sized suture constructions. However, the amount of tensile strength reduction observed when replacing a high strength UHMWPE end with a lower strength end is always less than expected as the replacement ends appear to cushion or insulate the UHMWPE ends from each other which leads to higher retained tensile strength from the remaining UHMWPE ends.

Since the invention is directed at improvements in the cover or outer sheath of the suture, this invention is applicable to both coreless sutures and sutures with cores. The cores can be of any construction including twisted or non-twisted multifilament, braided cores or monofilament cores. However, for most sizes of UHMWPE braided suture a coreless construction is preferred. This is because a coreless construction gives better knotting properties for sutures made from high modulus UHMWPE yarn. For other suture materials a core is normally needed to prevent the sheath from collapsing in suture sizes greater than about USP size 5-0 to a flat profile which is not optimum for suturing. The extremely high fiber modulus of UHMWPE of over 75 GPa is probably the main factor that keeps it from flattening during its handling, as opposed to the fiber modulus of about 3-10 GPa in other synthetic braided fibers. The coreless UHMWPE braid will flatten when it compressed by the forces knotting. This phenomenon contributes to its lower knot profile and improved knotting properties.

In the course of the experiments for this invention is has also been recognized that certain dyeing conditions of dye concentration, added acid concentrations, temperature and time of dyeing can sometimes yield UHMWPE fiber which contains some degree of shadowing or surface modification. In some cases, it appears the normal bright finish of the UHMWPE has been diminished. Accordingly it may be possible to also reduce the "glare" of the non-colored UHMWPE sutures by a surface modification technique. It is well known that the surface of polyethylene can be modified by chemical treatment, photochemical treatment, surface grafting, surface oxidation, halogenation, plasma, halogenation or corona treatment. The addition of shadowing to the UHMWPE surface appears to enhance the differentiation provided by the half dyed end of the suture of this invention. Thus, shadowing of fibers used in suture constructions may be an important property for distinguishing sutures.

The half dyeing process can be carried out by a number of different process methods. One of the preferred methods is to wind the suture on a frame and then dip half of it into a dye bath. Of course, the frames can be of a variety of sizes and configurations including flat, square, rectangular or round. For some sutures that dyeing could also take place on other devices or even in a skein form. The half dyeing process can also be carried out on pre-cut pieces of suture that are then half dyed in bundles of the sutures. Certainly other aids to enhance the dyeing process can be envisioned. For example, it has also been discovered that the junction between the half dyed end and the other end can also be improved by applying anti-wicking compounds like silicone fluids to the junction line before the dye dipping process.

The colored sutures of this invention can also be made by performing the half dyeing before the braiding process. In this method the colorless, but dyeable fiber is half dyed on a skein or a frame, and then transferred to a braider bobbin. The suture of this invention can then be made by braiding all three end types together on the braider. No additional dyeing step is necessary in this method. The procedures for mixing and using dye baths for the half and half process will generally follow those known to practitioners of the art. For example, in the green half dyeing an aqueous solution is prepared of D&C Green No. 5 at a concentration of about 0.02 to 0.2% by weight with an added concentration of about 2 to 10% of acetic acid. The dye bath is heated and half of the suture is dipped into the dye bath for a time period of about 5 to 120 minutes. The suture is rinsed of the excess dye, washed and dried for further processing.

It is also important to note that the palate of colors available to color sutures is strictly controlled, because sutures are an implantable device. Use of any unauthorized colorant is considered adulteration by the Color Division of the FDA. Colors for particular polymers must be listed in the Code of Federal Regulations (CFR). Therefore, colors or color combinations in sutures are extremely limited by FDA regulations and not by technology available to color polymers or fibers that are used to construct suture products.

Colorants available to provide color to polymers, fibers or braided yarns must be listed by the FDA and can be classified as either dyes or pigments. Pigments are not soluble in any solvents and must be compounded into the base polymer resin before it is extruded into either multifilament or monofilament yarn. Pigments can also be suspended in gel-like solutions to color gel spun fibers. Dyes can also be compounded into polymer resins or added to a molten polymer at the end of a polymerization. However, because dyes have solubility in solvent, they can be used to "solvent dye" fibers or braided yarns used to make sutures. Of course, this method is limited by the ability of the fiber to accept a particular dye. Higher crystalline polymer fibers like those of polypropylene or UHMWPE cannot be solvent dyed by normal methods. The FDA names certifiable dyes as either "FD&C" for solubility in water or "D&C" for solubility in organic solvents. Some D&C dyes, like D&C Green #5, do have limited amounts of solubility in water and can be used to dye fibers in aqueous solutions.

Table 1, below, lists examples of colorants for use in coloring the sutures.

TABLE 1

| SUTURE MATERIAL | COLORANT | COLORANT TYPE | Solvent Dye | MAX. WT % PERMITTED |
|---|---|---|---|---|
| Polyethylene | Cr—Co—Al Oxide | pigment | NO | 2.0 |
| Polypropylene | [Phthalocyaninato(2-)] copper | pigment | NO | 0.5 |
| Polyester (PET) | D&C Green #6 | dye | YES | 0.75 |
| Polyester (PET) | D&C Blue #6 | dye | YES | 0.2 |
| Nylon 66, Nylon 6 | D&C Green #5 | dye | YES | 0.6 |
| Nylon 66, Nylon 6 | Logwood Extract | dye | YES | 1.0 |
| Nylon 66, Nylon 6 | FD&C Blue #2 | dye | YES | 1.0 |
| Silk | Logwood Extract | dye | YES | 1.0 |
| PGA | D&C Green #6 | dye | NO | 0.1 |
| PGA | D&C Violet #2 | dye | NO | 0.2 |
| PGA-TMC | D&C Green #6 | dye | NO | 0.21 |
| PGA-PLA (90:10) | D&C Violet #2 | dye | NO | 0.2 |
| PLLA | None | NA | YES | NA |
| PDO | D&C Violet #2 | dye | NO | 0.3 |
| PDO | D&C Blue #6 | dye | NO | 0.5 |

Table 2, below, includes examples of various embodiments, for a USP size 2 suture having fourteen ends of 110 dtex UHMWPE yarn, of possible color combinations for non-absorbable and absorbable co-braids. However, some colorants included in this chart are not yet approved by the FDA for use in the polymers listed.

TABLE 2

| | Continuous 6-0 | | Dyeable | | |
|---|---|---|---|---|---|
| Example # | Fiber | Type | Fiber | Type | Half Dye Color |
| 1 | BLUE PP | 1E-MONO | CLR NYL | 1E-MONO | GRN NYL |
| 2 | BLK NYL | 1E-MONO | CLR NYL | 1E-MONO | GRN NYL |
| 3 | GRN NYL | 1E-MONO | CLR NYL | 1E-MONO | GRN NYL |
| 4 | BLUE UPE | 1E-MULTI | CLR NYL | 1E-MONO | GRN NYL |

TABLE 2-continued

|  | Continuous 6-0 | | Dyeable | | |
| --- | --- | --- | --- | --- | --- |
| Example # | Fiber | Type | Fiber | Type | Half Dye Color |
| 5 | BLUE PE | 1E-MONO | CLR NYL | 1E-MONO | GRN NYL |
| 6 | BLK NYL | 1E-MONO | CLR NYL | 1E-MONO | BLUE NYL |
| 7 | GRN PGA | 1E-MULTI | UND PLA | 1E-MULTI | VIOL PLA |
| 8 | BLUE PDO | 1E-MONO | UND PLA | 1E-MULTI | VIOL PLA |
| 9 | VIOL PDO | 1E-MONO | UND PLA | 1E-MULTI | GRN PLA |
| 10 | GRN PGT | 1E-MONO | UND PLA | 1E-MULTI | VIOL PLA |
| 11 | VIOL PGA | 1E-MULTI | UND PLA | 1E-MULTI | GRN PLA |
| 12 | GRN PGA | 1E-MULTI | UND PLA | 1E-MULTI | VIOL PLA |

Additionally, Table 3, below, details examples of braided, colored sutures in accordance with various embodiments of the present invention. The configurations in Table 3 are a subset of possible combinations described more fully in Table 5.

TABLE 3

Material configuration (UHMWPE w/CLR NYL & BLU PP)

| | | UHMWPE Yarn | | CLR NYL | | BLU PP | | |
| --- | --- | --- | --- | --- | --- | --- | --- | --- |
| Lot # | Size | dtex | # of ends | size | # of ends | size | # of ends | Pattern | Example |
| R-452 | 5 | 440 | 6 | 5-0 | 1 | 5-0 | 1 | Crossed | X X X X X X X |
| R-453 | 5 | 440 | 6 | 5-0 | 1 | 5-0 | 1 | In-line | / / / / / / / / / / |
| R-454 | 3/4 | 220 | 10 | 6-0 | 1 | 6-0 | 1 | Crossed | X X X X X X X |
| R-455 | 3/4 | 220 | 10 | 6-0 | 1 | 6-0 | 1 | In-line | / / / / / / / / / / |
| R-456 | 2 | 110 | 14 | 6-0 | 1 | 6-0 | 1 | Standard | // // // // // // |
| R-457 | 2 | 110 | 14 | 6-0 | 1 | 6-0 | 1 | Crossed | X X X X X X X |
| R-458 | 2 | 110 | 14 | 6-0 | 1 | 6-0 | 1 | In-line | / / / / / / / / / / |
| R-459 | 1 | 110 | 10 | 6-0 | 1 | 6-0 | 1 | Crossed | X X X X X X X |
| R-460 | 1 | 110 | 10 | 6-0 | 1 | 6-0 | 1 | In-line | / / / / / / / / / / |
| R-461 | 0 | 110 | 6 | 6-0 | 1 | 6-0 | 1 | Crossed | X X X X X X X |
| R-462 | 0 | 110 | 6 | 6-0 | 1 | 6-0 | 1 | In-line | / / / / / / / / / / |
| R-463 | 2-0 | 55 | 10 | 7-0 | 1 | 7-0 | 1 | Crossed | X X X X X X X |
| R-464 | 2-0 | 55 | 10 | 7-0 | 1 | 7-0 | 1 | In-line | / / / / / / / / / / |
| R-465 | 3-0 | 55 | 6 | 7-0 | 1 | 7-0 | 1 | Crossed | X X X X X X X |
| R-466 | 3-0 | 55 | 6 | 7-0 | 1 | 7-0 | 1 | In-line | / / / / / / / / / / |

Table 4, below, includes a key to the abbreviations used in Tables 1, 2, and 3. Given the number of suture materials and colorants available there are many other combinations possible.

TABLE 4

| | |
| --- | --- |
| BLUE PP: | Polypropylene monofilament with [phthalocyaninato(2–)] copper colorant. |
| VIOL PP: | Polypropylene monofilament with D&C Violet #2 colorant. |
| GRN PP: | Polypropylene monofilament with D&C Green #6 colorant. |
| CLR NYL: | Clear nylon monofilament. |
| BLK NYL: | Nylon monofilament with logwood extract colorant. |
| GRN NYL: | Nylon monofilament with D&C Green #5 colorant. |
| BLUE NYL: | Nylon monofilament with FD&C Blue #2 colorant. |
| BLUE UPE: | Blue UHMWPE multifilament with chromium-cobalt-aluminum oxide colorant. |
| BLUE PE: | Blue high density polyethylene (HDPE) monofilament with chromium-cobalt-aluminum oxide colorant. |
| UND PLA: | Undyed poly-L-lactic acid (PLLA) multifilament. |
| VIOL PLA: | Poly-L-lactic acid (PLLA) multifilament with D&C Violet #2 colorant. |
| GRN PLA | Poly-L-lactic acid (PLLA) multifilament with D&C Green #6 colorant. |
| BLUE PDO: | Polydioxanone monofilament with D&C Blue #6 colorant. |
| VIOL PDO: | Polydioxanone monofilament with D&C Violet #2 colorant. |
| GRN PGT: | Polyglycolic acid-trimethylene carbonate copolymer monofilament with D&C Green #6 colorant. |
| GRN PGA: | Polyglycolic acid multifilament with D&C Green #6 colorant. |

TABLE 4-continued

| | |
| --- | --- |
| VIOL PGA: | Polyglycolic acid multifilament with D&C Violet #2 colorant. |

Table 5, below provides additional details regarding another type of braid construction for sutures in accordance with various embodiments of the invention. Table 5 does not list the possible arrangements of the different fibers on bobbins to be set up on a braider machine that will give corresponding different arrangements of non-colored and colored fiber in the produced suture products, some of which by example were presented in Table 3. Additionally, there are numerous additional arrangements of non-colored and colored fibers that are possible, and the examples contained in Table 5 are not meant to limit the invention in any way. In Table 5, the "CLR Nylon size/dtex" refers to the at least one third end" of a dyeable fiber. The "colored size/dtex" refers to the "at least one second end" of a continuous colored fiber. The "size" listed for use in the dyeable and continuous fibers is an estimate of the size of the ends based upon USP diameter ranges needed to braid the suture of the invention. However, dependent on other factors, such as handling properties or surgeon's preferences, either larger or smaller ends can be used in braiding.

TABLE 5

| USP Size | Total # Ends = N | Max # Ends UHMWPE N − 2 | Max # Ends clear/colored N/2 | UHMWPE Yarn dtex | # of ends | CLR Nylon size size | //dtex dtex | # of ends | colored size size | /dtex dtex | # of ends |
|---|---|---|---|---|---|---|---|---|---|---|---|
| 5 | 8 | 6 | 4 | 440 | 6 | 5-0 | 110-220 | 1 | 5-0 | 110-220 | 1 |
| 5 | 8 | 6 | 4 | 440 | 5 | 5-0 | 110-220 | 2 | 5-0 | 110-220 | 1 |
| 5 | 8 | 6 | 4 | 440 | 4 | 5-0 | 110-220 | 3 | 5-0 | 110-220 | 1 |
| 3/4 | 12 | 10 | 6 | 220 | 10 | 6-0 | 55-110 | 1 | 6-0 | 55-110 | 1 |
| 3/4 | 12 | 10 | 6 | 220 | 9 | 6-0 | 55-110 | 2 | 6-0 | 55-110 | 1 |
| 3/4 | 12 | 10 | 6 | 220 | 8 | 6-0 | 55-110 | 3 | 6-0 | 55-110 | 1 |
| 3/4 | 12 | 10 | 6 | 220 | 7 | 6-0 | 55-110 | 4 | 6-0 | 55-110 | 1 |
| 3/4 | 12 | 10 | 6 | 220 | 6 | 6-0 | 55-110 | 5 | 6-0 | 55-110 | 1 |
| 2 | 16 | 14 | 8 | 110 | 14 | 6-0 | 55-110 | 1 | 6-0 | 55-110 | 1 |
| 2 | 16 | 14 | 8 | 110 | 13 | 6-0 | 55-110 | 2 | 6-0 | 55-110 | 1 |
| 2 | 16 | 14 | 8 | 110 | 12 | 6-0 | 55-110 | 3 | 6-0 | 55-110 | 1 |
| 2 | 16 | 14 | 8 | 110 | 11 | 6-0 | 55-110 | 4 | 6-0 | 55-110 | 1 |
| 2 | 16 | 14 | 8 | 110 | 10 | 6-0 | 55-110 | 5 | 6-0 | 55-110 | 1 |
| 2 | 16 | 14 | 8 | 110 | 9 | 6-0 | 55-110 | 6 | 6-0 | 55-110 | 1 |
| 2 | 16 | 14 | 8 | 110 | 8 | 6-0 | 55-110 | 7 | 6-0 | 55-110 | 1 |
| 1 | 12 | 10 | 6 | 110 | 10 | 6-0 | 55-110 | 1 | 6-0 | 55-110 | 1 |
| 1 | 12 | 10 | 6 | 110 | 9 | 6-0 | 55-110 | 2 | 6-0 | 55-110 | 1 |
| 1 | 12 | 10 | 6 | 110 | 8 | 6-0 | 55-110 | 3 | 6-0 | 55-110 | 1 |
| 1 | 12 | 10 | 6 | 110 | 7 | 6-0 | 55-110 | 4 | 6-0 | 55-110 | 1 |
| 1 | 12 | 10 | 6 | 110 | 6 | 6-0 | 55-110 | 5 | 6-0 | 55-110 | 1 |
| 0 | 8 | 6 | 4 | 110 | 6 | 6-0 | 55-110 | 1 | 6-0 | 55-110 | 1 |
| 0 | 8 | 6 | 4 | 110 | 5 | 6-0 | 55-110 | 2 | 6-0 | 55-110 | 1 |
| 0 | 8 | 6 | 4 | 110 | 4 | 6-0 | 55-110 | 3 | 6-0 | 55-110 | 1 |
| 2-0 | 12 | 10 | 6 | 55 | 10 | 7-0 | 20-55 | 1 | 7-0 | 20-55 | 1 |
| 2-0 | 12 | 10 | 6 | 55 | 9 | 7-0 | 20-55 | 2 | 7-0 | 20-55 | 1 |
| 2-0 | 12 | 10 | 6 | 55 | 8 | 7-0 | 20-55 | 3 | 7-0 | 20-55 | 1 |
| 2-0 | 12 | 10 | 6 | 55 | 7 | 7-0 | 20-55 | 4 | 7-0 | 20-55 | 1 |
| 2-0 | 12 | 10 | 6 | 55 | 6 | 7-0 | 20-55 | 5 | 7-0 | 20-55 | 1 |
| 3-0 | 8 | 6 | 4 | 55 | 6 | 7-0 | 20-55 | 1 | 7-0 | 20-55 | 1 |
| 3-0 | 8 | 6 | 4 | 55 | 5 | 7-0 | 20-55 | 2 | 7-0 | 20-55 | 1 |
| 3-0 | 8 | 6 | 4 | 55 | 4 | 7-0 | 20-55 | 3 | 7-0 | 20-55 | 1 |

In the braid construction detailed in Table 5, the total number of ends is represented by "N." The maximum number of ends made from ultra-high molecular weight polyethylene is "N-2," and the maximum number of ends that are clear is N/2.

The many features and advantages of the invention are apparent from the detailed specification, and thus, it is intended by the appended claims to cover all such features and advantages of the invention which fall within the true spirit and scope of the invention. Further, because numerous modifications and variations will readily occur to those skilled in the art, it is not desired to limit the invention to the exact construction and operation illustrated and described, and accordingly, all suitable modifications and equivalents may be resorted to falling within the scope of the invention.

What is claimed is:

1. A suture comprising:
    a woven braid of fibers including:
        a first fiber comprising a colorable material, wherein an entire length of the first fiber is colored a first color; and
        a second fiber comprising a colorable material, wherein only a portion of the second fiber is colored a second color; and
        a third fiber.

2. The suture of claim 1, wherein the third fiber comprises ultra-high molecular weight polyethylene, and the third fiber is white or clear.

3. The suture of claim 2, wherein the first fiber and the second fiber comprise at least one of polypropylene, nylon, polyethylene, and polyester.

4. The suture of claim 1, wherein each of the first, second, and third fibers has a distinct color, and the third fiber is white or clear.

5. The suture of claim 1, wherein at least one of the fibers is at least partly blue, and at least one of the fibers is at least partly green.

6. The suture of claim 1, wherein the second fiber is colored only about halfway along a length.

7. The suture of claim 1, wherein one or both of the first and second fibers are co-plied with the third fiber.

8. The suture of claim 1, wherein the first color, the second color, and a color of the third strand are different from each other.

9. The suture of claim 1, wherein each of the first fiber, the second fiber, and the third fiber comprises a monofilament or a multifilament.

10. A method of manufacturing a suture comprising:
    weaving a braid of fibers including a first fiber comprising a colorable material, a second fiber comprising a colorable material, and a third fiber;
    coloring an entire length of the first fiber a first color; and
    coloring only a portion of the second fiber a second color.

11. The method of claim 10, wherein the first fiber and the portion of the second fiber are colored before weaving the braid.

12. The method of claim 10, wherein the first fiber is colored before the first fiber is woven into the braid, and the portion of the second fiber is colored after the second fiber is woven into the braid.

13. The method of claim 10, further comprising coloring a second portion of the second fiber a third color.

14. The method of claim 10, further comprising dipping at least a half of the suture into a dye bath.

15. The method of claim 10, wherein the third fiber comprises ultra-high molecular weight polyethylene.

16. The method of claim 10, further comprising co-plying one or both of the first and second fibers with the third fiber.

17. The method of claim 10, further comprising co-plying one or both of the first and second fibers on a braider bobbin with the third fiber.

18. The method of claim 10, wherein the first color, the second color, and a color of the third end are different from each other.

19. The method of claim 10, wherein each of the first fiber, the second fiber, and the third fiber comprises a monofilament or a multifilament.

20. The method of claim 10, wherein coloring only a portion of the second fiber a second color includes coloring about half of a length of the second fiber the second color.

21. A suture comprising:
- a woven braid of fibers including:
  - a first fiber comprising a colorable material, wherein an entire length of the first fiber is colored a first color; and
  - a second fiber comprising a colorable material, wherein only a portion of the second fiber is colored a second color.

22. The suture of claim 21, wherein one or both of the first and second fibers are monofilaments co-plied with a third fiber.

23. The suture of claim 21, one or both of the first and second fibers are multifilaments co-plied with a third fiber.

24. The suture of claim 21, further comprising a third fiber comprising ultra-high molecular weight polyethylene, wherein one or both of the first and second fibers comprises at least one of polypropylene, nylon, polyethylene, and polyester.

25. The suture of claim 21, wherein each of the first fiber and the second fiber comprises a monofilament or a multifilament.

26. The suture of claim 21, wherein about half of a length of the second fiber is colored the second color.

* * * * *